(12) United States Patent
Sharma et al.

(10) Patent No.: US 6,818,613 B2
(45) Date of Patent: Nov. 16, 2004

(54) AQUEOUS SUSTAINED-RELEASE FORMULATIONS OF PROTEINS

(75) Inventors: Basant Sharma, Bridgewater, NJ (US); Renzhe Jin, Bridgewater, NJ (US); Sunitha Rudolph, Doylestown, PA (US); Wing K. Cheung, Warren, NJ (US); Selima Begum, Edison, NJ (US); Marian Kelley, Annandale, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/037,369

(22) Filed: Nov. 7, 2001

(65) Prior Publication Data

US 2003/0148938 A1 Aug. 7, 2003

(51) Int. Cl.[7] ............................................... A61K 38/16
(52) U.S. Cl. .......................................................... 514/8
(58) Field of Search ............................................. 514/8

(56) References Cited

U.S. PATENT DOCUMENTS

| | | | |
|---|---|---|---|
| 3,865,801 A | * | 2/1975 | Chiba et al. |
| 4,465,624 A | * | 8/1984 | Chiba et al. |
| 4,548,952 A | * | 10/1985 | Casas |
| 4,596,806 A | * | 6/1986 | Ishikawa et al. |
| 4,705,805 A | * | 11/1987 | Yamada et al. |
| 4,717,717 A | | 1/1988 | Finkenaur |
| 5,457,093 A | | 10/1995 | Cini et al. |
| 5,503,827 A | * | 4/1996 | Woog et al. |
| 5,643,575 A | | 7/1997 | Martinez et al. |
| 5,674,534 A | | 10/1997 | Zale et al. |
| 5,688,679 A | | 11/1997 | Powell |
| 5,716,644 A | | 2/1998 | Zale et al. |
| 5,747,446 A | * | 5/1998 | Sytkowski |
| 5,919,758 A | * | 7/1999 | Sytkowski |
| 6,107,272 A | * | 8/2000 | Sytkowski |

FOREIGN PATENT DOCUMENTS

| | | |
|---|---|---|
| EP | 0640619 | 3/1995 |
| EP | 1064951 | 1/2001 |
| WO | WO 8301198 A | 4/1983 |
| WO | WO 94/12650 | 6/1994 |
| WO | WO 96/40073 | 12/1996 |
| WO | WO 9707788 A | 3/1997 |
| WO | WO 9728828 A | 6/1997 |
| WO | WO 98/05363 | 2/1998 |
| WO | WO 99/05268 | 2/1999 |
| WO | WO 99/11781 | 3/1999 |
| WO | WO 99/15154 | 4/1999 |
| WO | WO 99/38890 | 8/1999 |
| WO | WO 99/66054 | 12/1999 |
| WO | WO 0013710 A | 3/2000 |
| WO | WO 00/38651 | 7/2000 |
| WO | WO 0061169 A | 10/2000 |

OTHER PUBLICATIONS

Ritchey et al., Blood, vol. 57, No. 4, 1981, 788–793.*
Ford et al., "Fusion Tails for the Recovery and Purification of Recombinant Proteins", *Protein Expression and Purification* (1991) 2:95–107.
A. J. Bailer, "Testing for the Equality of Area Under the Curves When Using Destructive Measurement Techniques", *J. Pharmacokinetics Biopharmaceutics* (Jun. 1988) 16(3): 303–309.
PCT International Search Report, PCT/US02/36300, Mar. 19, 2003.
Cheung, W. et al: "Pharmacokinetics and pharmacodynamics of epoetin alfe once weekly and three times weekly", European Journal of Clinical Pharmacology, vol. 57, No. 5, Aug. 2001, pp. 411–418, ISSN: 0031–6970.
Troxel, T.R., et al: "Ovulation and reproductive hormones following steriod pretreatment, calf removal and GnRH in postpartum suckled beef cows". Joournal of Animal Science, vol. 51, No. 3, 1980, pp. 652–659. ISSN:0021–8812.

* cited by examiner

*Primary Examiner*—Michael Meller

(57) ABSTRACT

The present invention is directed to sustained-release pharmaceutical formulations of therapeutic proteins containing carboxymethyl ether cellulose polymer and methods of manufacture and use thereof.

6 Claims, 8 Drawing Sheets

AQUEOUS SUSTAINED-RELEASE FORMULATIONS OF PROTEINS

FIELD OF THE INVENTION

The present invention provides aqueous sustained-release pharmaceutical formulations of therapeutic proteins containing carboxymethyl ether cellulose polymer and their method of manufacture. The present invention also provides methods to use the pharmaceutical formulations that provide a variety of new benefits, including greater efficacy, safety, patient convenience, and patient compliance.

BACKGROUND OF THE INVENTION

Due to recent advances in genetic and cell engineering technologies, proteins known to exhibit various pharmacological actions in vivo are capable of production in large amounts for pharmaceutical applications. A major limitation of the development of protein therapeutics is the preparation of stable pharmaceutical formulations of the proteins. Therapeutic proteins are typically administered by frequent injection because the active agent protein generally has short in vivo half-lives and negligible oral bio-availability, thus posing a significant physical burden on the patient and associated administrative costs. As such, there is currently a great deal of interest in developing and evaluating sustained-release formulations. Effective sustained-release formulations can provide a means of controlling blood levels of the active ingredient, and also provide greater efficacy, safety, patient convenience and patient compliance.

To date there have been mainly two mechanisms to achieve sustained-release of a protein therapeutic: 1) modifying the protein to increase the half-life of the protein, typically by reducing the clearance rate; and 2) preparing sustained-release formulations of protein encapsulated in polymer microspheres. The advantage to generating sustained release formulations is that the formulation could theoretically be utilized for many protein therapeutics.

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.).

U.S. Pat. Nos. 5,674,534 and 5,716,644 and PCT publication WO 96/40073 describe a polymeric matrix containing particles of erythropoietin that are stabilized against aggregation with a salt.

Unfortunately, the instability of most proteins (e.g. denaturation and loss of bioactivity upon exposure to heat, organic solvents, etc.) has greatly limited the development and evaluation of sustained-release formulations thereof. In addition these techniques are not as broadly applicable as generally anticipated due to the biochemical variability in protein that greatly influences any individual protein tolerance for the conditions required to produce microspheres.

PCT publication WO 00/38651 describes a pharmaceutical composition containing a protein in a polymeric matrix that has thermally and pH responsive gelation/de-gelation properties. These formulations may be prepared without exposure to heat or organic solvents, but are characterized by their use of modified hydrogels. The use of thermostable hydrogels suffers by undesirable difficulties of manufacture and thus is currently commercially impractical. Another undesirable characteristic of these modified hydrogels is that their biocompatibility or immunogenicity is poorly characterized.

U.S. Pat. No. 4,717,717 to A. L. Finkenaur describes compositions of epidermal growth factor that are stabilized against loss of biological activity by the presence of a cellulose polymer. There is no description of in vivo sustained release properties of these formulations.

U.S. Pat. No. 5,457,093 to Cini et al. describes gel formulations containing growth factors used in ophthalmic and topical applications. There is no description of the use of these formulations for parenteral administration, nor is there any suggestion that these formulations would have sustained release properties in vivo.

There remains a need, therefore, for parenteral sustained-release formulations of erythropoietin that can be manufactured easily and promote the stability of active agent protein contained therein.

SUMMARY OF THE INVENTION

The present invention provides a method to prepare aqueous sustained-release pharmaceutical formulations of therapeutic proteins for parenteral administration. The present invention also provides pharmaceutical formulations for general use with proteins for parenteral administration comprising:

a) a pharmaceutically active amount of a protein;
b) a pharmaceutically acceptable pH buffering agent to provide a pH in the range of about pH 4.5 to about pH 9;
c) a tonicity agent in the concentration range of about 0 to about 125 millimolar; and
d) Sodium carboxymethyl ether cellulose in the concentration range of about 0.5% to about 7% total formula weight;

wherein the pH of the aqueous formula is about 4.5 to about pH 9.0.

A preferred formulation of the present invention provides a pharmaceutical formulation of erythropoietin comprising:

a) a pharmaceutically active amount of erythropoietin;
b) a pharmaceutically acceptable pH buffering agent to provide a pH in the range of about pH 6 to about pH 9;
c) a tonicity agent in the concentration range of about 0 to about 200 millimolar; and
d) sodium carboxymethyl ether cellulose (CMC) in the concentration range of about 0.5% to about 7% total formula weight, said CMC having a molecular weight in the range of about 50,000 daltons to about 1,000,000 daltons;

wherein the pH of the formulation is about pH 6.3 to about pH 8.3.

The present invention also provides a method to prepare aqueous sustained-release pharmaceutical formulations of erythropoietin comprising admixing an aqueous solution of a CMC polymer with a pharmaceutically active amount of EPO. The formulations of the present invention utilize CMC polymer that is primarily in a solution state rather than in a micro-particulate state.

The present invention also provides methods to use these sustained-release formulations comprising dosing regimens where the formulation is administered at a wide variety of desired intervals, including, but not limited to, thrice per two weeks, once per week, once per two weeks, once per three weeks, once monthly, once per five weeks, once per six weeks, or at any other time interval or combination of time intervals that may be desirable for the particular patient.

DETAILED DESCRIPTION OF THE INVENTION

Figure 1:
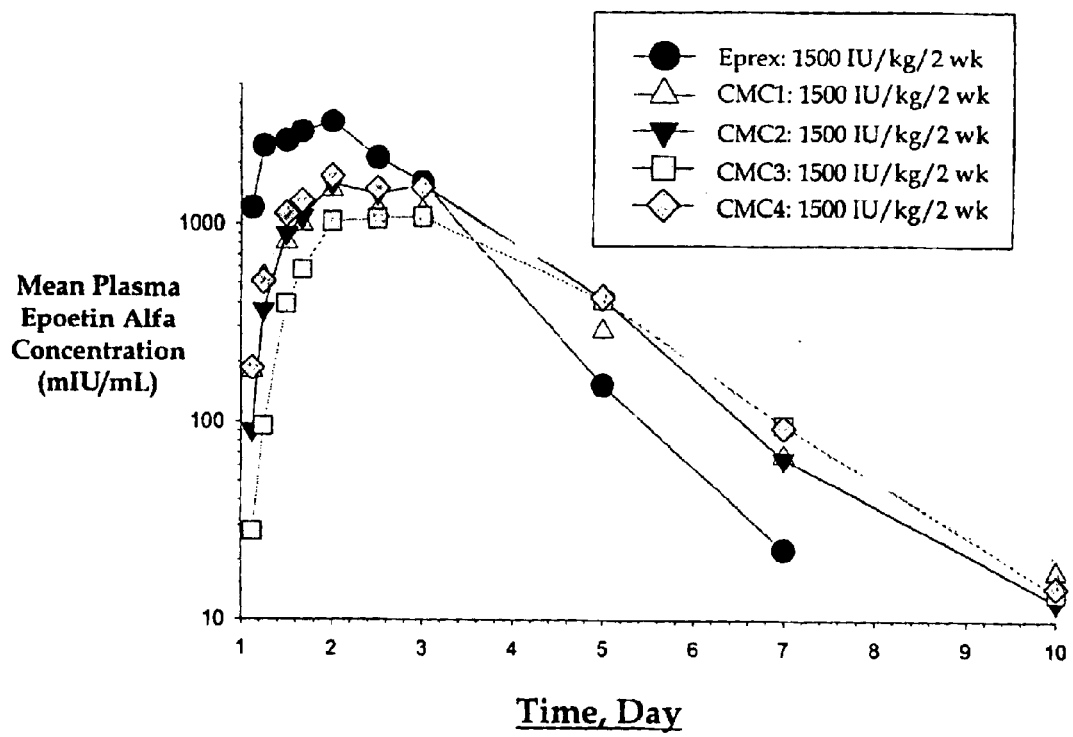
FIG. 1: Pharmacokinetics of sustained-release formulations CMC-1, CMC-2, CMC-3, CMC-4 illustrated as mean Plasma Epogen Alfa concentration versus time.

As used herein, "erythropoietin" or "EPO" shall include those polypeptides and proteins that have the biological activity of recombinant human erythropoietin (rhEPO), as well as erythropoietin analogs, erythropoietin isoforms, erythropoietin mimetics, erythropoietin fragments, hybrid erythropoietin proteins, fusion proteins oligomers and multimers of the above, homologues of the above, glycosylation pattern variants of the above, and muteins of the above, regardless of the biological activity of same, and further regardless of the method of synthesis or manufacture thereof including, but not limited to, recombinant (whether produced from cDNA or genomic DNA), synthetic, transgenic, and gene activated methods. Specific examples of erythropoietin include, Epoetin alfa (EPREX®, ERYPO®, PROCRIT®), novel erythropoiesis stimulating protein (NESP™, ARANESP™, darbepoetin alfa) such as the hyperglycosylated analog of recombinant human erythropoietin (Epoetin) described in European patent application EP640619, human erythropoietin analog (such as the human serum albumin fusion proteins described in the international patent application WO9966054), erythropoietin mutants described in the international patent application WO9938890, erythropoietin omega, which may be produced from an Apa I restriction fragment of the human erythropoietin gene described in U.S. Pat. No. 5,688,679, altered glycosylated human erythropoietin described in the international patent application WO9911781 and EP1064951, PEG conjugated erythropoietin analogs described in WO9805363 or U.S. Pat. No. 5,643,575. Specific examples of cell lines modified for expression of endogenous human erythropoietin are described in international patent applications WO9905268 and WO9412650. The generally preferred form of EPO is purified recombinant human EPO (rhEPO), currently formulated and distributed under the trademarks of EPREX®, ERYPO®, PROCRIT® or ARANESP™.

As used herein, the term "protein" includes peptides, polypeptides, consensus molecules, analogs, derivatives or combinations thereof. The term "protein" embraces polypeptide sequences containing modified amino acids and glycoproteins, or proteins that contain at least one serine, threonine, or arginine side chain bearing a carbohydrate moiety. Also included are those polypeptides with amino acid substitutions that are "conservative" according to acidity, charge, hydrophobicity, polarity, size or any other characteristic known to those skilled in the art. See generally, Creighton, *Proteins,* W. H. Freeman and Company, NY (1984) pp. 498. Generally one may make one or more changes in selected amino acids so long as such a change preserves the overall biological activity of the protein. Small amino terminal extensions, such as an amino-terminal methionine or serine residue, a small linker peptide of up to about twenty to twenty-five residues, or a small extension that facilitates purification, such as a polyhistidine tract, an antigenic epitope or a binding domain, may also be present. See, in general, Ford et al., *Protein Expression and Purification* (1991) 2:95–107. Polypeptides or analogs thereof may also contain one or more amino acid analogs, such as peptidomimetics. One skilled in the art will readily be able to adapt a desired protein active agent to the compositions of present invention.

The term "subject" as used herein, refers to an animal, preferably a mammal, most preferably a human, who is the object of treatment, observation or experiment.

The amount of protein used in the formulations of the present invention will vary with the biological potency of the protein as well as the desired potency of the formulation, but will generally contain about 1 µg/ml to about 2000 µg/ml protein per formulation. Specifically the erythropoietin-containing formulations of the present invention may contain a "pharmaceutically active amount of erythropoietin", generally about 1000 IU/ml to about 180,000 IU/ml of erythropoietin, wherein 120,000 IU is approximately 1000 µg. The erythropoietin may be provided as an aqueous solution of a bulk reagent that is diluted into the formulation of the present invention or may be provided as a dried reagent and reconstituted using the appropriate amount of the aqueous formulation. Dried reagents include, for example, lyophilized or spray-dried erythropoietin. Where erythropoietin is provided as a bulk reagent in formulations of high potency (e.g. greater than 100,000 IU/ml), it is preferable that the erythropoietin bulk reagent be provided in a phosphate buffered solution. This is due to increased patient discomfort caused by high concentrations of citric acid buffers typically used in the preparation of recombinant human erythropoietin. Buffer exchange is achieved using methods well known in the art, such as diafiltration or dialysis to provide an EPO bulk that contains less than 1 millimolar citrate.

The amount of buffering agent useful in the pharmaceutical compositions of the present invention depends largely on the particular buffer used and the desired pH of the formulation. The concentration of buffering ions will generally range from about 10 mM to about 30 mM. Suitable buffer systems to maintain the pH range of about four to about nine include, but are not limited to, sodium citrate/citric acid, sodium acetate/acetic acid, sodium or potassium phosphate dibasic/monobasic, and any other pharmaceutically acceptable pH buffering agent(s) known in the art. The use of a buffer system of sodium phosphate dibasic and sodium phosphate monobasic is preferred. A pH-adjusting agent such as, but not limited to, hydrochloric acid, citric acid, sodium hydroxide, or a salt of any of these, in particular sodium citrate, may be added to the formulations to adjust the formulation pH to within the desired formulation pH range. One goal for these formulations is to minimize the patient discomfort associated with subcutaneous administration of the citrate-buffered formulations. Therefore phosphate buffer systems are particularly preferred in all formulations of the present invention, both in the aqueous protein bulk reagent and in the formulation buffer component.

The preferred pH range for the protein-containing formulations of the present invention is between about pH 4.5 to about pH 9, preferably in the range of about pH 6 to about pH 7.5. The preferred pH range for the erythropoietin-containing formulations of the present invention is between about pH 6.5 to about pH 8, preferably in the range of about pH 6.9 to about pH 7.4.

One or more ionic tonicity agents may be used in the formulations of the present invention. An ionic tonicity agent is any agent capable of rendering the formulations of the present invention iso-osmotic or nearly iso-osmotic with human blood and carries a positive or negative charge in aqueous solutions. Typical suitable tonicity agents are well known in the art, and include but are not limited to sodium chloride, potassium chloride, ammonium sulfate, glycine, or other amino acids. The preferred tonicity agents of the present invention include, but are not limited to, NaCl, KCl, and glycine, said agent being used at a concentration in the range of about 0 to about 170 millimolar. Use of sodium chloride as a tonicity agent is preferred in the formulations of the present invention at a concentration of about 75 mM to about 100 mM. The type of tonicity agent and its concentration may influence the sustained-release properties of the formulation. In formulations containing more than one tonicity agent, the total concentration of tonicity agents is generally less than 200 mM.

Sodium carboxymethyl ether cellulose (CMC-CAS # 9004-32-4) having a molecular weight of about 50,000 to 1,000,000 is used in the formulations of the present invention in the concentration range of 0.5% to about 7% total formula weight, preferably from about 0.5% to about 2%, and most preferably at about 2%. The concentration of CMC used is varied based on the identity of and amount of the protein used in the formulation. The sustained-release activity of the formulation is tested by comparing pharmacokinetic properties of a CMC containing formulation to an otherwise identical formulation lacking CMC. Formulations containing 0.5% to about 2% CMC are generally preferred due to their ease of manufacture and because of the ease of administration by injection. Generally there is a relationship between the amount of protein in the formulation, the amount of CMC in the formulation, and the pharmacokinetic properties of the formulation. Formulations containing more protein require higher amounts of CMC to provide sustained release properties. The amount of protein/CMC may be expressed as a ratio of protein (in micrograms) to % CMC (grams per 100 mL). Preferred formulations of EPO contain a ratio less than or equal to 660 μg EPO/% CMC.

The phrase "sustained release" as used herein refers to beneficial pharmacokinetic properties of the formulation. Pharmacokinetic parameters may be calculated using methods known in the art or as described herein. For example, but not by way of limitation, one or more pharmacokinetic parameters may be calculated by model independent methods using WinNonlin software, Version 1.1 (Scientific Consulting, Incorporation, Apex, N.C.). Various pharmacokinetic properties may be considered when evaluating the sustained-release properties of a formulation of the present invention. For example, but not by way of limitation, the following PK parameters may be evaluated to determine the sustained-release properties of the formulations of the present invention:

Peak serum concentration ($C_{max}$): The observed maximum serum concentration of the protein. A sustained-release formulation may have a lower $C_{max}$ than a similar non-sustained release formulation due to slower absorption into circulation.

Time to $C_{max}$ ($t_{max}$): The time at which $C_{max}$ occurs. A sustained-release formulation may have a longer $T_{max}$ than a similar non-sustained release formulation due to slower diffusion into circulation.

Terminal half-life ($t_{1/2}$): A sustained release formulation may have a longer $t_{1/2}$ than a similar non-sustained release formulation.

Without being limited by theory, the inventors contemplate that the sustained-release properties of these formulations occur through a combination of hydrophobic interaction of the protein with the CMC and an ionic interaction between the protein and CMC. At the pH described, both the protein and the CMC carry a negative charge, and thus another component, possibly the charged tonicity agent, forms an "ionic bridge", similar to a salt-bridge as is well-known in biochemical interactions. The interaction between the protein, CMC and/or the ionic tonicity agent is sufficiently strong to retard diffusion of the protein from the injection site without being permanently retained at the site. It is readily apparent to those of ordinary skill in the art that the formulations of the present invention are generally applicable to parenteral administration of therapeutic proteins other than erythropoietin, including, but not limited to, interferons, granulocyte colony stimulating factor, insulin, antibodies and antibody fragments, somatotropin, tissue plasminogen activator, interleukins, and antigens for immune responses.

The formulations of the present invention utilize CMC polymer that is primarily in a solution state rather than in a micro-particulate state, however a wide variety of ratios of micro-particulate CMC polymer to non-microparticulate CMC polymer may be suitable for use in the formulations of the present invention.

Proteins and polypeptides suitable for use in the present invention include, but are not limited to, insulin, motilin, gastrin, prolactin, adrenocorticotropic hormone (ACTH), erythropoietin, growth hormone (GH), kerantinocyte growth factor (KGF), stem cell factor (SCF), thrombopoietin, osteoprotegerin (OPG), and obesity protein (OB protein: protein may also be referred to herein as leptin), granulocyte colony-stimulating factor (G-CSF), alpha interferon (in particular alpha 2b), beta interferon (in particular beta 1a and beta 1b), gamma interferon, interleukin 2, fibroblast growth factors (FGF), insulin-like growth factors (IGFs), macrophage colony stimulating factor (M-CSF), granulocyte macrophage colony stimulating factor (GM-CSF), colony simulating growth factors (CSFs), tumor necrosis factor (TNF), thyroid stimulating hormone (TSH), luteinizing hormone (LH), follicle stimulating hormone (FSH), human chorionic gonadotropin (HCG), neurotrophic growth factor (NGF), neurotrophic factor 3 (NT3), neurotrophic factor 4 (NT4), brain-derived neurotrophic factor (BDNF), glial cell line derived neurotrophic factor (GDNF), platelet-derived growth factor (PGDF: also known as interleukin 11), vascular endothelial growth factor (VEGF), bone morphogenetic protein (BMP), megakaryocyte growth differentiation factor (MGDF), Factor VII, Factor VIIa, Factor VIII, Factor IX, superoxide dismutase (SOD), tissue plasminogen activator (TPA), urokinase, streptokinase, kallikrein, alpha-galactosidase, Pancreatic Rnase, platelet activting factor acetylhydrolase, interleukin-1 receptor antagonist (IL-Ira), REMICADE (Infliximab: a monoclonal antibody that blocks the biological activity of circulating TNFα ENBREL (etanercept: dimeric fusion protein consisting of the extracellular ligand-binding portion of the human 75 kilodalton (p75) tumor necrosis factor receptor (TNFR) linked to Fc portion of human IgG1).

The formulations of the present invention are prepared by admixing the formulation reagents in an aqueous solution such that the components are mixed substantially uniformly so that none of the components are localized. Advantageously all of the formulation components, except the protein component, can be prepared and adjusted to conditions suitable for the protein prior to the addition of the protein component. Alternatively, the protein bulk reagent may be diafiltered into an appropriate buffer system, preferably phosphate buffer, and the other reagents may be added to the protein bulk, and the bulk protein concentration can be adjusted appropriately to the desired potency.

A preferred method of formulation for erythropoietin-containing formulations of the present invention, as well as other protein-containing formulations generally, comprises the steps:
a) difiltering a recombinant human EPO bulk solution against a 10 to 30 millimolar phosphate buffer to provide a phosphate buffered EPO bulk containing less than 1 mM citric acid;
b) admixing a quantity of CMC to the phosphate buffered EPO bulk sufficient to provide a final concentration of about 0.5% to about 7% CMC;
c) admixing a quantity of NaCl to the phosphate buffered EPO bulk sufficient to provide a final concentration of about 0 mM to about 170 mM NaCl; and
d) adjusting the EPO bulk with water sufficient to provide a predetermined final formulation volume and EPO potency.

The formulations of the present invention are administered to a subject in need thereof via parental administration excluding intravenous administration. Particular routes of parenteral administration include, but are not limited to, intramuscular, subcutaneous, intraperitoneal, intracerebral, intraventricular, intracerebroventricular, intrathecal, intracisternal, intraspinal and/or peri-spinal routes of administration by delivery via intracranial or intravertebral needles and/or catheters with or without pump devices. The route of administration may be selected based on the therapeutic indication of the pharmaceutically active protein.

Hormones, cytokines, coagulation factors, and other biologically active proteins including insulin, motilin, gastrin, prolactin, adrenocorticotropic hormone (ACTH), erythropoietin (EPO), growth hormone (GH), stem cell factor (SCF), thrombopoietin, osteoprotegerin (OPG), and obesity protein (OB protein: OB protein may also be referred to herein as leptin), granulocyte colony-stimulating factor (G-CSF), alpha interferon (in particular alpha 2b), beta interferon (in particular beta 1a and beta 1b), gamma interferon, interleukin 2, insulin-like growth factors (IGFs), macrophage colony stimulating factor (M-CSF), granulocyte macrophage colony stimulating factor (GM-CSF), colony simulating growth factors (CSFs), tumor necrosis factor (TNF), thyroid stimulating hormone (TSH), luteinizing hormone (LH), follicle stimulating hormone (FSH), human chorionic gonadotropin (HCG) vascular endothelial growth factor (VEGF), megakaryocyte growth differentiation factor (MGDF), Factor VII, Factor VIIa, Factor VIII, Factor IX, superoxide dismutase (SOD), tissue plasminogen activator (TPA), urokinase, streptokinase, kallikrein, alpha-galactosidase, Pancreatic Rnase, platelet activting factor acetylhydrolase, interleukin-1 receptor antagonist (IL-Ira), REMICADE and ENBREL may be administered via intramuscular, subcutaneous, or intraperitoneal routes such that there is a systemic release of the protein.

Certain growth factors, such as kerantinocyte growth factor (KGF), fibroblast growth factors (FGF), platelet-derived growth factor (PGDF: also known as interleukin 11), may be administered at or near a site of action to achieve a localize benefit. Local injection of the formulation of the present invention may result in higher local-area concentrations of the active pharmaceutical reagent and may be more efficacious than topical administration of medicinal gels containing these proteins.

Neurologically active proteins, including erythropoietin (EPO), neurotrophic growth factor (NGF), neurotrophic factor 3 (NT3), neurotrophic factor 4 (NT4), brain-derived neurotrophic factor (BDNF), glial cell line derived neurotrophic factor (GDNF), bone morphogenetic protein (BMP) may be administered directly into neuronal tissue by intracerebral, intraventricular, intracerebroventricular, intrathecal, intracisternal, intraspinal and/or peri-spinal routes of administration by delivery via intracranial or intravertebral needles and/or catheters with or without pump devices.

As used for administration of EPO, the phrase "therapeutically effective" is generally from about 1 to 10000 I.U./kg, preferably from about 50 to 2000 I.U./kg, more preferably from about 50 to 600 I.U./kg, and most preferably from about 50 to 300 I.U./kg body weight especially when erythropoietin is administered subcutaneously. Advantageously, the formulations of the present invention may be administered to a responding subject at any desired frequency or time interval between administrations without reduced efficacy. In a preferred dosing regimen, the subject is administered the sustained release formulations of the present invention thrice per two weeks, once per week, once per two weeks, once per three weeks, once per month, once per five weeks, once per six weeks, or at more frequent or less frequent intervals, or at any combination of frequencies or time intervals as desired. The effective daily dosing of erythropoietin (EPO) is preferably from about 4000 to about 9000 I.U. (equivalent to about 60,000 I.U. to about 120,000 I.U. every two weeks). Most preferably the effective daily dosing of erythropoietin (EPO) is 5715 I.U. (equivalent to about 80,000 I.U. every two weeks). A preferred dosing regimen may be once per three weeks, particularly for subjects receiving chemotherapy for the treatment of cancer, since many chemotherapeutic regimens are administered on a once per three-week schedule. However, any dosing schedule of a therapeutic protein, such as EPO, formulated according to the present invention, can be easily coordinated with regular visits to the treating physician or with the dosing schedule of another agent, such as an anti-tumor agent, as is desirable for the patient. This allows the EPO regimen and the chemotherapeutic regimen to be administered simultaneously or in parallel, providing an economic and desirable benefit for the subject. EPO administration is delayed or withheld if the patient, male or female, exhibits a hemoglobin level in excess of about 18 g/dL for a human male and about 16 g/dL for a human female.

The following examples are provided for the purpose of illustrating the present invention, without, however, limiting the present invention to the illustrative examples.

EXAMPLE 1

Evaluation of EPO Sustained Release Formulations in Immunosuppressed Dogs

This study was designed to evaluate CMC-EPO in beagle dogs during various dosing regimens. Pharmacodynamics and pharmacokinetic profiles of EPO (erythropoietin) formulations were also examined.

Formulations

EPREX: (Control formulation)

CMC 1: 15,000 IU EPO, 0.5% CMC, 10 mM NaPhosphate buffer, pH 7, 15 mg/ml Glycine; Total tonicity=199 mg Pro/% CMC=250

CMC 2: 15,000 IU EPO, 1.0% CMC, 10 mM NaPhosphate buffer, pH 7, 15 mg/ml Glycine; Total tonicity=199 mg Pro/% CMC=125

CMC 3: 15,000 IU EPO, 2.0% CMC, 10 mM NaPhosphate buffer, pH 7, 15 mg/ml Glycine; Total tonicity=199 mg Pro/% CMC=63

CMC 4: 15,000 IU EPO, 2.0% CMC, 10 mM NaPhosphate buffer, pH 7, 50 mg/ml Mannitol; Total tonicity=274 mg Pro/% CMC=63

Storage

EPO formulations were stored refrigerated (~4° C.) protected from light when not used on study.

| Study Animals | |
|---|---|
| Species: | Dog |
| Strain: | Beagle |
| Sex: | Male |
| Source: | Harlan Sprague Dawley, Inc. Indianapolis, Indiana 46299 |
| Age at Dosing: | 9 to 18 months |
| Target Weight at First Dosing: | 6 to 18 kg |
| Identification Method: | Tattoo applied by animal supplier. |
| Number on Study: | 21 (N = 3 dogs/group) |

Housing

Dogs were group housed in a dog holding room and acclimated to handling and sample collection prior to dose administration. Quarantine was held at least five days prior to dose administration. At the end of the quarantine period, the health of all animals was confirmed by study personnel. During the study/collection period, the dogs were group housed unless necessary due to health conditions. Housing rooms were labeled with the animals' and protocol numbers.

Environmental Conditions

Animal rooms were maintained at 23±3° C. with a relative humidity of 50±15% and a twelve-hour light/dark cycle. There were at least ten room air changes per hour.

Diet and Water

Dogs had access to Purina Certified Canine Diet® #5007 and water ad libitum when on study.

Study Design (Summary)

Beagle dogs (N=3 dogs per group, 7 groups) were randomly assigned to treatment groups. On Day −2, the dogs were administered a single oral dose of cyclosporin (25 mg/kg). Thereafter, the dogs received a daily maintenance dose of cyclosporin (10 mg/kg). All formulations and vehicle were administered subcutaneously (sc).

Preparation and Test Formulations Dose Administration: (Day 1)

Test and control formulations were administered to the dogs on Day 1 (all formulations administered at the volume specified in the following table). The dose was drawn-up into a syringe fitted with appropriate gauge needle. The subcutaneous dose was administered in the dorsal neck region. Dose sites were clipped prior to dosing and marked with indelible ink.

| EPO Dose (IU/kg) | Formulations | Amount to be Injected | Volume to be Injected |
|---|---|---|---|
| 1,500 Days 1 and 15 | Eprex | 15,000 IU—every 2 weeks | 1 mL/animal |
| 1,500 Days 1 and 15 | CMC 1 | 15,000 IU—every 2 weeks | 1 mL/animal |
| 1,500 Days 1 and 15 | CMC 2 | 15,000 IU—every 2 weeks | 1 mL/animal |
| 1,500 Days 1 and 15 | CMC 3 | 15,000 IU—every 2 weeks | 1 mL/animal |
| 1,500 Days 1 and 15 | CMC 4 | 15,000 IU—every 2 weeks | 1 mL/animal |

Observations Sample Collection, and Processing

At designated primary time points (see below), approximately 2 mL of blood was collected via the jugular vein into heparinized Vacutainers®. In case of jugular vein failure, blood was collected via the cephalic vein and noted. The primary blood collection, obtained prior to cyclosporin administration, was used to harvest plasma. The blood was placed on ice, centrifuged (1500×g, for ten minutes at approximately 4° C.), and plasma collected. Plasma will be frozen at −20° C. until analysis.

At the secondary blood collection, approximately 2 mL of blood collected using a Vacutainer® containing EDTA was obtained in the morning and placed on ice. The secondary collection was stored at approximately 4° C. as whole blood and used for reticulocyte, hemoglobin, and total red blood cell measurements.

Primary Blood Collection Time Points:

Day 1 (pre-dose, 3, 6, 12, and 16 hours), Day 2 (24 and 36 hours) Day 3, Day 5, Day 7, Day 10, Day 15 (pre-dose), Day 16, and Day 28.

Secondary Blood Collection Time Points:

Pre-dose on Days 1, 3, 7, 10, 14, 17, 21, 24, and 28

Data Analysis

Excel (Microsoft®, Version 97-SR-2) was used for data processing. WinNonlin (Scientific Consulting®, Version 2.1) was used for processing plasma data and calculating the following pharmacokinetic parameters: $C_{max}$, $T_{max}$, terminal $T_{1/2}$, and Cl/F (Note: the fraction of dose absorbed cannot be estimated, therefore clearance for this model is actually clearance/F, where F is the fraction of dose absorbed). WinNonlin was also be used to calculate $AUC_{(0-last)}$ (of the differences from the baseline) for reticulocyte, hemoglobin, and red blood cell data. Applicable statistical analyses (i.e., ANOVA, t-test) were conducted.

Results

As seen in FIG. 1, all formulations containing CMC had superior pharmacokinetic properties compared to EPREX. Notably, the $C_{max}$ was lower than EPREX and the $T_{1/2}$ was longer than that for EPREX.

Figure 2:
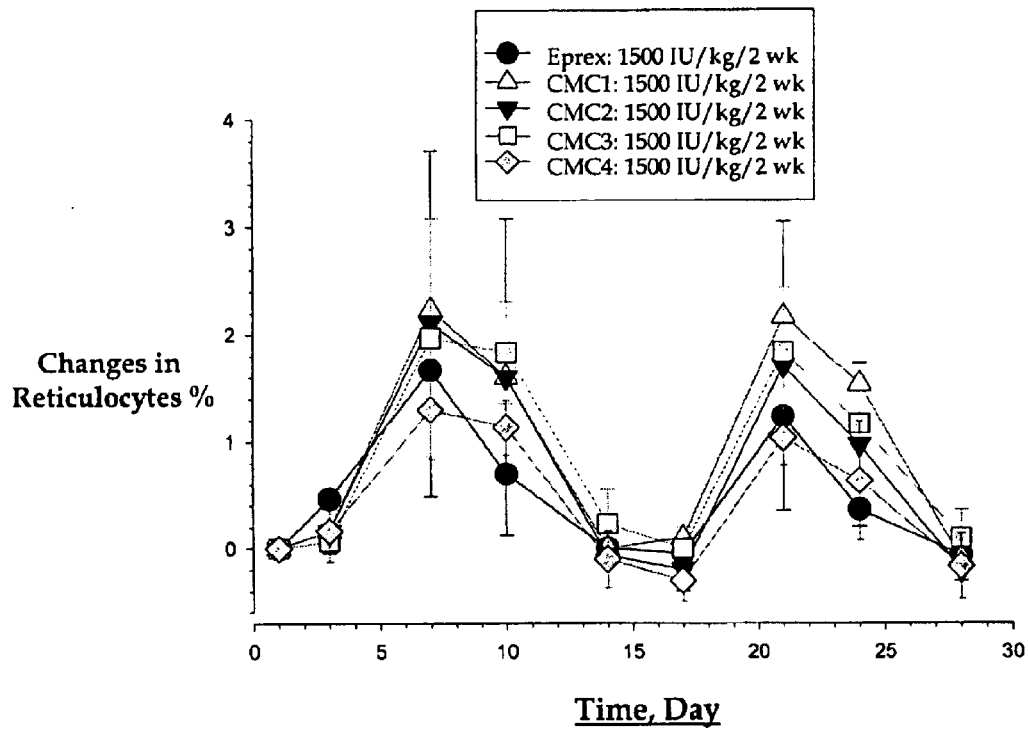
FIG. 2: Pharmacodynamics of sustained-release formulations CMC-1, CMC-2, CMC-3, CMC-4 illustrated as change in the percentage reticulocytes versus time.
Figure 3:
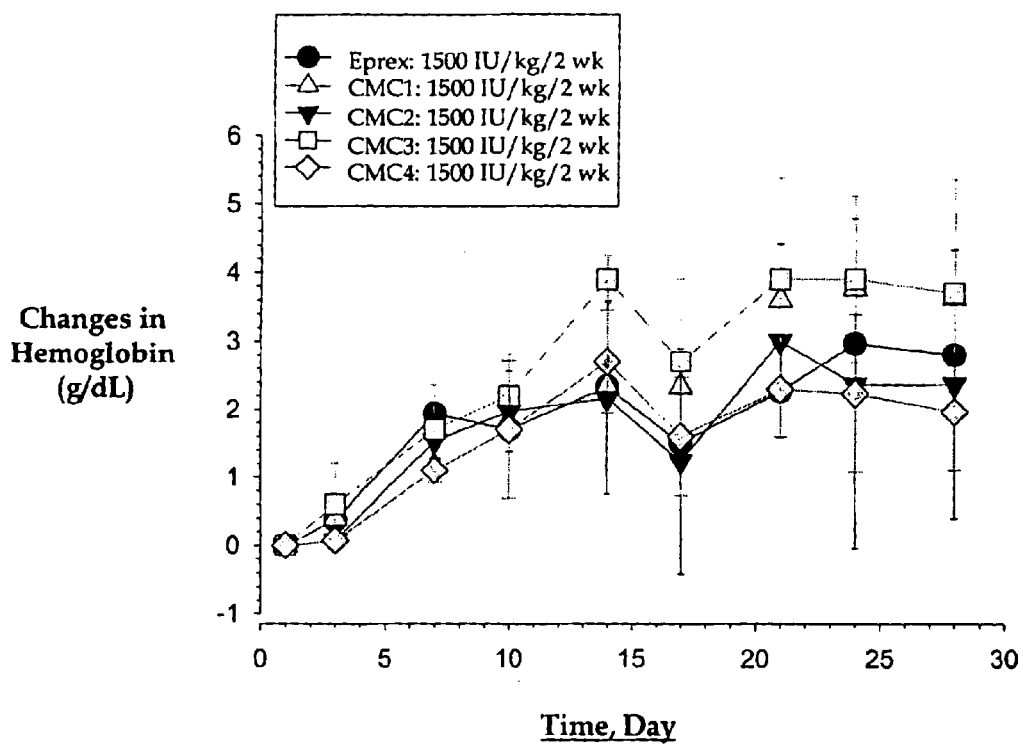
FIG. 3: Pharmacodynamics of sustained-release formulations CMC-1, CMC-2, CMC-3, CMC-4 illustrated as change in the amount of Hemoglobin versus time.
Figure 4:
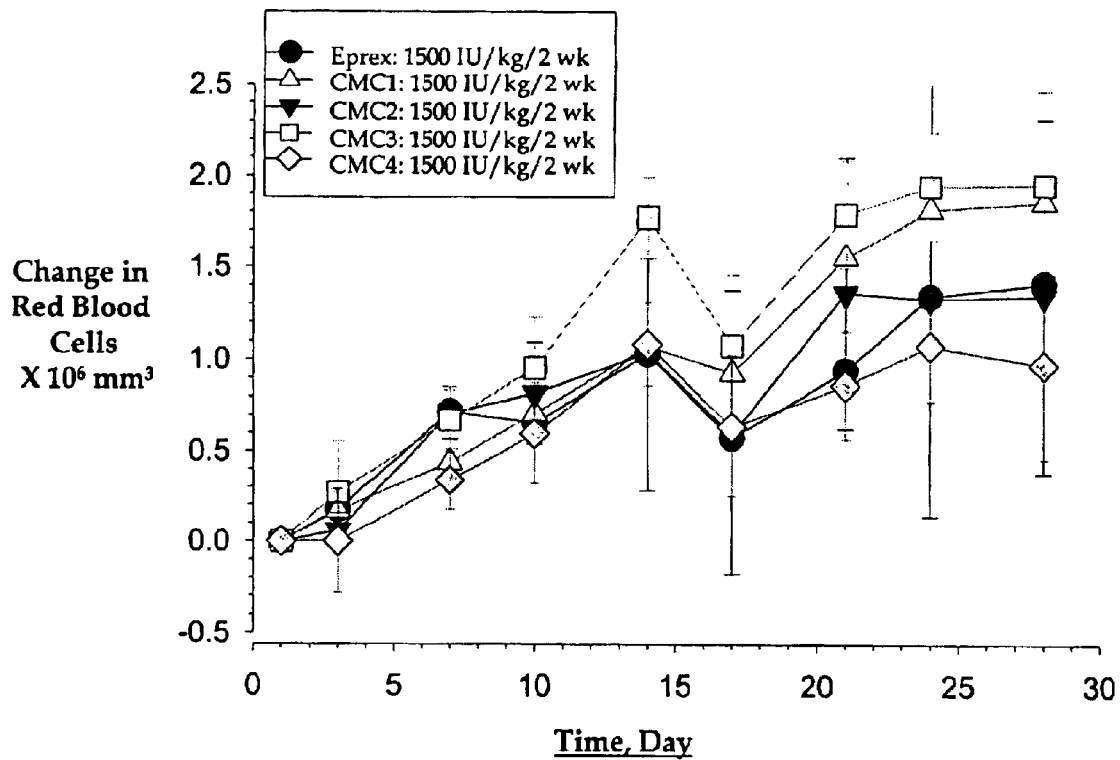
FIG. 4: Pharmacodynamics of sustained-release formulations CMC-1, CMC-2, CMC-3, CMC-4 illustrated as change in the number of red blood cells versus time.
Figure 5:
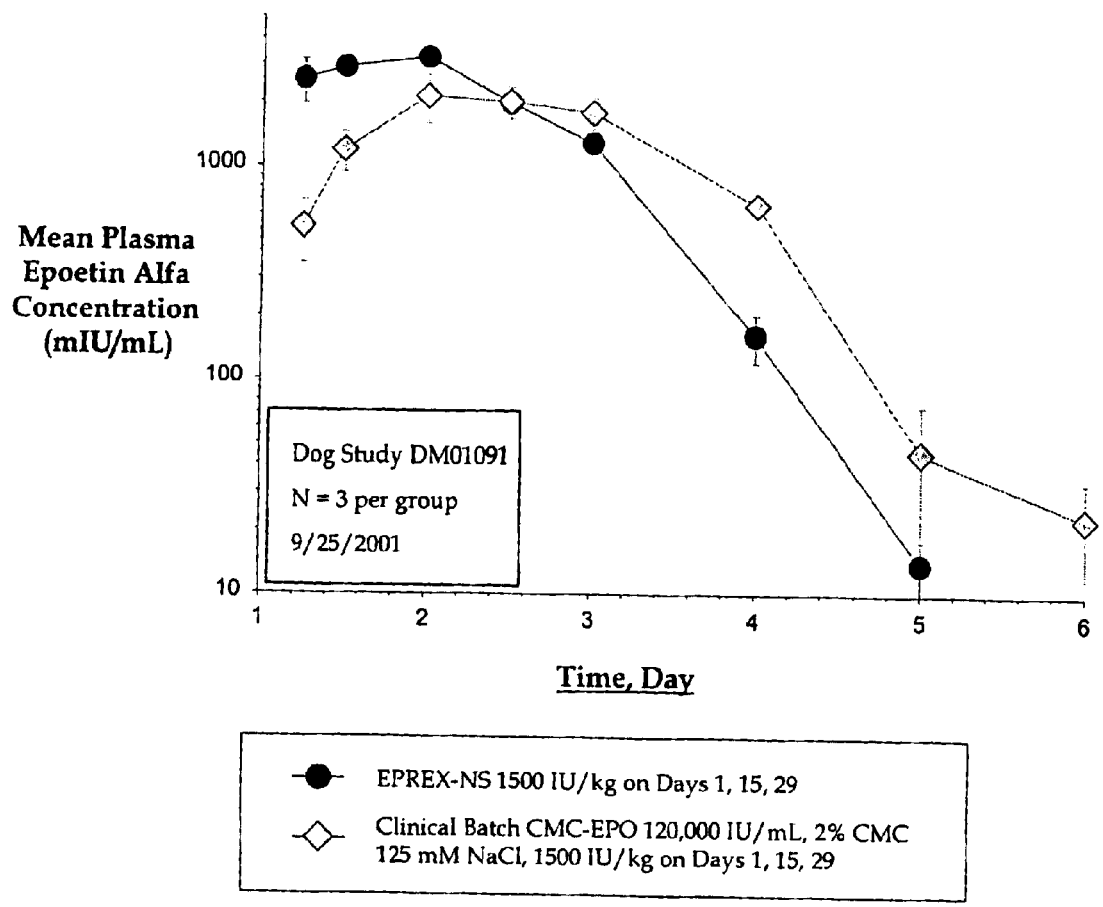
FIG. 5: Pharmacokinetics of Clinical Batch CMC-EPO illustrated as mean Plasma Epoetin Alfa concentration versus time.
Figure 6:
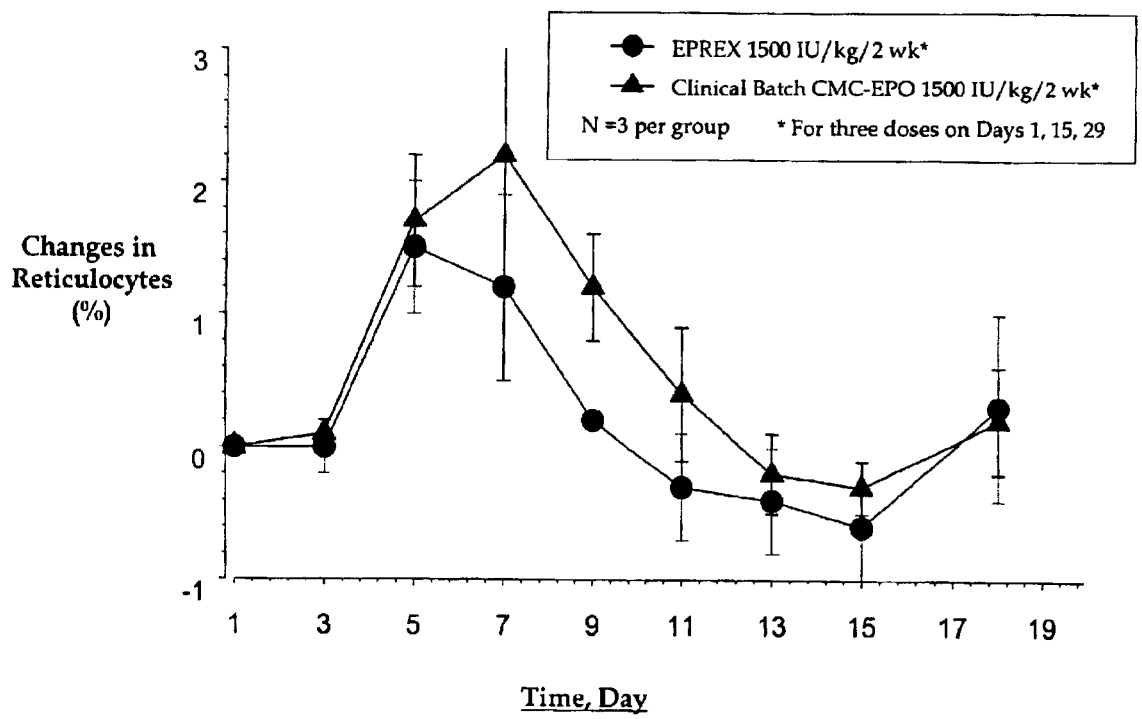
FIG. 6: Pharmacodynamics of Clinical Batch CMC-EPO illustrated as change in the percentage of reticulocytes versus time.
Figure 7:
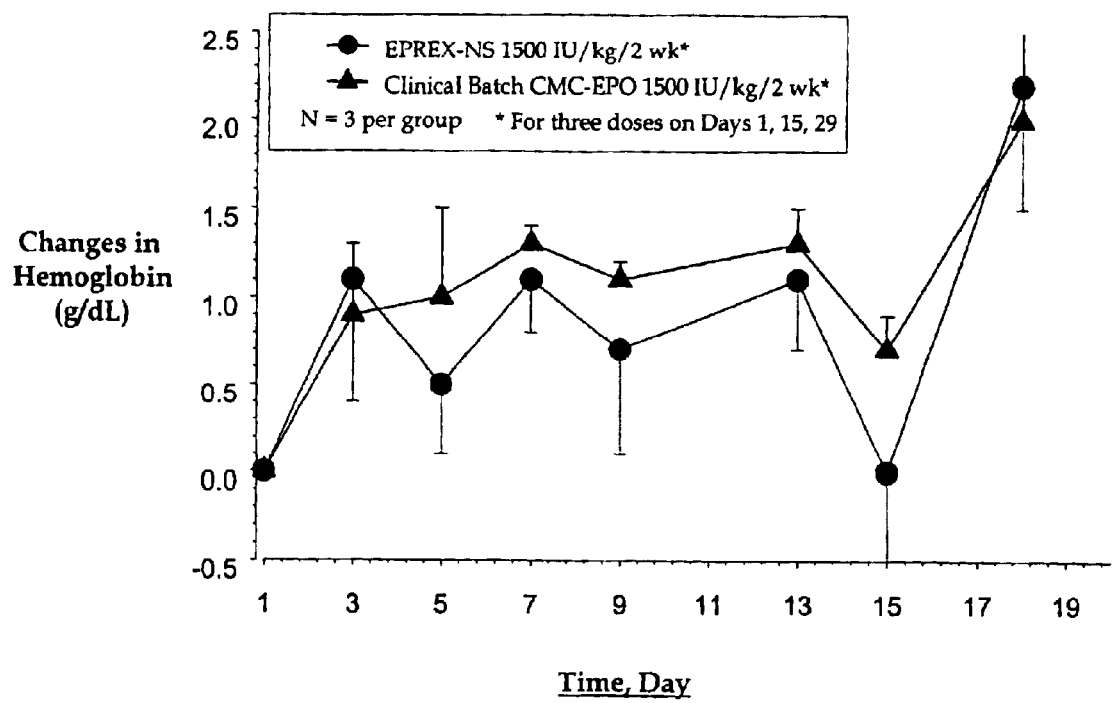
FIG. 7: Pharmacodynamics of Clinical Batch CMC-EPO illustrated as change in the amount of Hemoglobin versus time.
Figure 8:
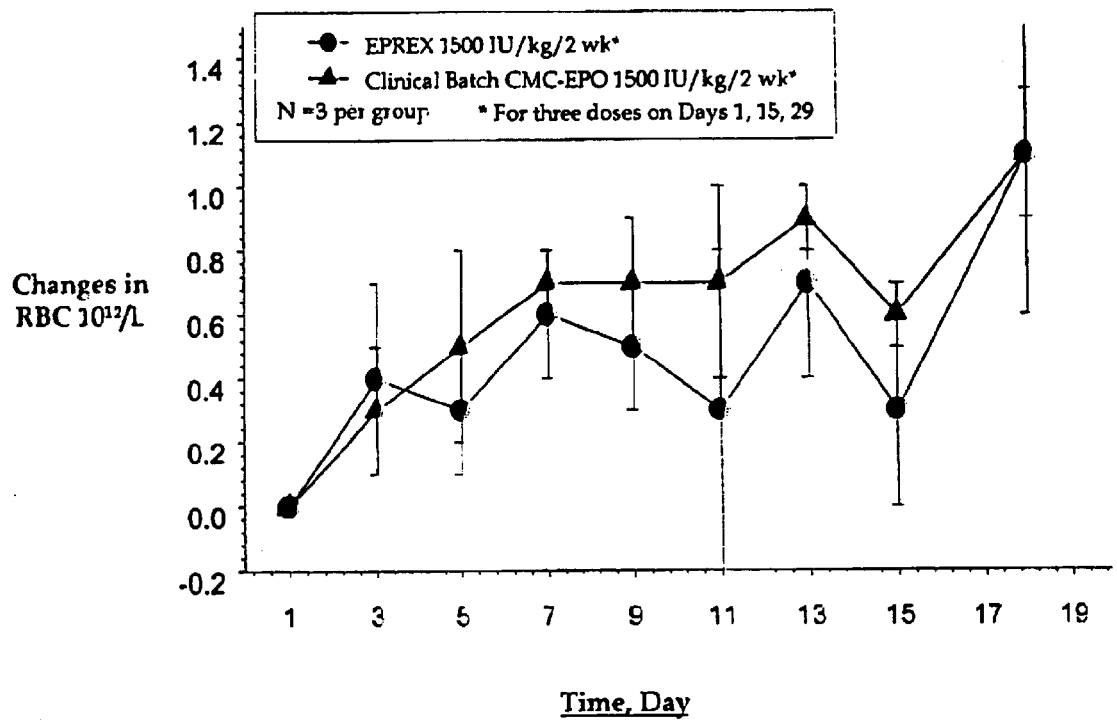
FIG. 8: Pharmacodynamics of Clinical Batch CMC-EPO illustrated as change in the number of red blood cells versus time.

As seen in FIGS. 2, 3, and 4, the pharmacodynamic properties of all CMC formulations, except the formulation containing 50 mg/ml mannitol, were superior to EPREX. The formulation containing 50 mg/ml mannitol was similar to EPREX. FIG. 2 demonstrates a higher percent change in reticulocytes following administration of the CMC formulations. Also seen in FIG. 2 is a sharp increase and subsequent decrease for EPREX following administration of the drug. The decrease is mitigated in all of the CMC formulations, demonstrative of the amount of systemic EPO released from the injection site of these formulations. FIGS. 3 and 4 demonstrate the change in Hemoglobin and red blood cell (RBC) versus time. Except for the CMC formulations containing 50 mg/ml mannitol and 1% CMC, all other CMC formulations provided superior pharmacodynamic effects of stimulating hematopoiesis in the dogs.

EXAMPLE 2

Evaluation of EPO Formualtions in Immunosuppressed Dogs for One-Month Following Subcutaneous Administration Study Design (Summary)

This study was conducted analogously to that described in Example 1, modified as described herein. Beagle dogs (N=3 dogs/group, 5 groups) were randomly assigned to treatment groups. On Day −2, the dogs were administered a single oral dose of cyclosporin (25 mg/kg). Thereafter, the dogs received a daily maintenance dose of cyclosporin (10 mg/kg). Two dosing regimens were examined in immunosuppressed dogs. Both formulations and vehicle were administered in a single subcutaneous (sc) dose. At designated times over a four-week period, blood samples were collected. The injection site was monitored daily and body weights were obtained weekly.

Results

The CMC-5 formulation demonstrated superior pharmacokinetic properties to EPREX, characterized by a lower $C_{max}$ and a longer $T_{1/2}$. This formulation also demonstrated to have slightly better pharmacodynamic properties than EPREX.

EXAMPLE 3

Evaluation of a CMC-EPO Formulation Following Subcutaneous Dosing Every Three Weeks in Non-Immunosuppressed Male Beagle Dogs Formulation CMC-6: 80,000 IU/mL EPO, 1% CMC, 20 mM Na Phosphate pH 7.2, 100 mM NaCl; Total tonicity=100 mM µg Pro/% CMC=660

EPREX: 80K 80,000 IU/mL dose

Study Overview

The test and control articles were administered by multiple subcutaneous injections to beagle dogs, one injection per three-week period.

| | | Dose | | | | | | |
|---|---|---|---|---|---|---|---|---|
| | | EPO | | | | | Number of Animals (Male) | |
| Group | Treatment | Dose (IU/kg) | Volume (mL/kg) | Strength (IU/mL) | Total | Dose Days | Pharmacokinetic Sample Days | Pharmacodynamic Sample Days |
| 1 | CMC-6 | 1200 | 0.015 | 80,000 | 3 | 1, 22 | 1, 2, 3, 3.5, 4, 4.5, 5, 7, 10, 15, 22, 23, 28, 36 and 42 | 1, 3, 7, 10, 14, 17, 21 24, 28, 31, 35, 38 and 42 |
| 2 | Eprex | 1200 | 0.015 | 40,000 | 3 | 1, 22 | 1, 2, 3, 3.5, 4, 4.5, 5, 7, 10, 15, 22, 23, 28, 36 and 42 | 1, 3, 7, 10, 14, 17, 21, 24, 28, 31, 35, 38 and 42 |

*Pharmacokinetic samples were be collected on the days specified. On Day 1 samples were collected pre-dose then 6, 12, 24 (Day 2), and 36 hours post-dose. Single samples were collected on all other days at approximately the same time each day.

Formulations

EPREX: 40,000 dose

CMC: 5 40,000 IU EPO, 7% CMC, 20 mM Na Phosphate buffer, pH 7, 5 mg/ml Glycine (0.5%), 75 mM NaCl, 0.3% Tween 80. Total tonicity=142 mM µg Pro/% CMC=47

Preparation and Test Formulations Dose Administration: (Day 1)

All formulations were administered at the volume specified in the following table. Dose was drawn-up into a syringe fitted with appropriate gauge needle. The subcutaneous dose was administered in the dorsal neck region. Dose sites were clipped prior to dosing and marked with indelible ink.

| Treatments | EPO Dose (IU) | Dose Volume (mL) | Dose Route |
|---|---|---|---|
| EPREX | 30,000 | 0.75 | subcutaneous |
| CMC-5 | 30,000 | 0.75 | subcutaneous |

Primary Blood Collection Time Points:
All Groups: Pre-dose, 6, 12, and 16 hours on Day 1; 24 and 36 hours on Day 2; and Pre-dose on Days 3, 5, 7, 13, 17, 21, 24, and 28.

Secondary Blood Collection Time Points:
All Groups: Pre-dose on Days 1, 3, 7, 10, 14, 17, 21, 24, and 28.

Pharmacokinetics

The maximum mean plasma concentrations ($C_{max}$) and their times of occurrence ($T_{max}$) of EPO were determined. The areas under the mean plasma concentration-time curves from time zero to Day 22 ($AUC_{0-T}$), and their variances, was estimated by the linear trapezoidal rule according to Bailer, J. Pharmacokin. Biopharm., (1988) 16:303–309. Apparent clearance (CL/F) was estimated by dividing $AUC_{0-T}$ by dose (1200 IU/kg). Where appropriate, terminal rate constants (k) were estimated by fitting a linear regression of log mean concentration against time using data points randomly distributed about a single straight line. Terminal half-lives were calculated as ln2/k.

Pharmacodynamics

Blood for hematology studies (approximately 0.5 mL) was collected into tubes containing EDTA anticoagulant as described in the preceding table.

The following hematological properties were determined to evaluate the pharmacodynamic properties of the CMC-6 and control formulations:

Erythrocyte Count
Hemoglobin
Leukocyte Count (total)
Reticulocyte Count (absolute and percentage)
Reticulocyte Hemoglobin The changes from baseline in the pharmacodynamic parameters (% reticulocytes, hemoglobin, total red blood cells) was calculated using the value on Day 1 as the baseline value. The AUC of the change in pharmacodynamic values from baseline was calculated using linear trapezoidal rule.

Results

The pharrnacokinetics of CMC-6 demonstrated a lower $C_{max}$ and a lower $T_{1/2}$ than EPREX control. The pharmacodynamics of CMC-6 demonstrated a superior change in reticulocyte production by Day 6, but similar pharmacodynamic properties to EPREX in all other measures.

EXAMPLE 4

43-DAY Pharmacokenetic/Pharmacodynamic Study Following Subcutaneous Administration of EPO Formulations in Non-Immunosuppressed Male Beagle Dogs This study was designed to assess the pharmacokinetics and pharmacodynamics of the test articles in the male beagle dog administered via subcutaneous injection.

| Test System | |
|---|---|
| Species/breed: | beagle dogs |
| Supplier: | Marshall Farms, 5800 Lake Bluff Road North Rose, New York 14516 |
| Number of animals in the study: | 18 males |
| Age (approximate) at initiation of treatment: | 5 to 7 months |
| Body weight range (approximate) at initiation of treatment: | 8 to 11 kg |

This study was conducted in dogs to evaluate different formulations of EPO (Epoetin alfa), designed to maintain treatment-related erythropoiesis, which are for potential registration with regulatory agencies for therapeutic use in humans. The number of dogs used was the minimum number necessary to provide scientifically valid results for each of the formulations examined. No acceptable in vitro models are available. Purpose-bred beagle dogs are routinely used for the conduct of pharmacokinetic, pharmacodynamic, and toxicological studies to meet regulatory requirements.

Animal Husbandry

Housing: one room for the study, in an air-conditioned building:
temperature: 19 to 25° C. (target range)
relative humidity: >40 %,
air changes: minimum ten air changes per hour,
lighting cycle: twelve hours light (artificial)/twelve hours dark.
Caging: animals housed singly in pens (1.44 m²).
Diet: pelleted complete commercial diet (Diet 125C1, UAR); analyzed for the absence of chemical and bacteriological contaminants.
Quantity distributed: 300 g/animal/day (food offered after dosing on treatment days and at approximately the same time of day on other study days).
Water: mains drinking water, ad libitum, analyzed at least once a year for chemical contaminants and at least twice a year for bacterial contaminants (Laboratoire Santé Environnement Hygiène de Lyon).
Contaminants: no contaminants known to be present in the diet or water at levels which might interfere with achieving the objective of the study. Certificates of analysis for the diet and for the water will be maintained in the archives of the testing facility.

Pre-Treatment Procedures

Animal health procedure:
Standard canine vaccination and anti-parasite treatment performed by the supplier
Clinical examination for ill-health on arrival;
Full clinical examination during the acclimatization period.
Acclimatization period:
Two week minimum between animal arrival and start of treatment.
Identification of the animals:
Using tattoo on the pinna and microchip implants: Electronic Laboratory Animal System, ELAMS (Bio Medic Data Systems).

| Group Number | Color Code | Animal Numbers |
|---|---|---|
| 1 | White | 271 to 272 |
| 2 | Green | 274 to 276 |
| 3 | Blue | 277 to 279 |
| 4 | Red | 280 to 282 |
| 5 | Yellow | 283 to 285 |
| 6 | Salmon | 286 to 288 |

Experimental Design

Allocation to treatment group: performed during the acclimatization period: random allocation procedure based on body weight classes.

Animals were assigned to the following groups:

| Group | Epoetin alfa Dose (IU/kg/administration) | | | Number of Males |
|---|---|---|---|---|
| | Day 1 | Day 15 | Day 29 | |
| 1 | 1500 | 1500 | 1500 | 3 |
| 2 | 1500 | 1500 | 1500 | 3 |
| 3 | 1500 | 1500 | — | 3 |
| 4 | 1500 | 1500 | — | 3 |
| 5 | 1500 | 1500 | — | 3 |
| 6 | 1500 | 1500 | — | 3 |

Administration of the Test Articles

Route: subcutaneous
Method:
bolus injection using a sterile syringe and needle introduced subcutaneously after local disinfection with an aqueous solution of ethyl alcohol. One injection site in the dorsal cervical/interscapular regions was used.
Volume administered:
Individual dose volumes were calculated on the day of treatment to two decimal places according to the latest recorded body weight. The syringes containing the dosing solution were weighed before and after administration in order to calculate the actual individual delivered dose.
Frequency: Once on the day of treatment (Day 1).
Observations
Morbidity/Mortality:
Animals were observed at least twice daily. Any animal judged to be in a moribund condition will be bled for haematological, clinical chemistry and pharmacokinetic determinations and then euthanized.

Clinical Signs

Animals were observed daily. During the treatment period, animals were examined before and at least once after dosing to detect any clinical signs or reaction to treatment. The injections sites were observed daily. A full clinical examination were performed before the initiation of treatment.

Body Weight: Individual weighing once weekly, starting two weeks before initiation of treatment.

Clinical Laboratory Determinations

Blood Collection:

Blood was withdrawn from the jugular vein of the unanaesthetized, manually restrained animal.

Collection of samples

Haematology parameters: EDTA.

Clinical Chemistry parameters: without anticoagulant.

Haematology

All animals: twice prior to dosing (Day-7 and prior to dosing on Day 1), and on Days 3, 5, 7, 9, 11, 13, 15, 18, 21, 24, 27, 30. Animals from Groups 1 and 2 will additionally be bled on days 33, 36, 39 and 43.

Approximately 2 ml of whole blood will be taken from each dog per time point.
Hemoglobin
Red Blood Cell Count
Mean Corpuscular Volume
Reticulocyte Count (absolute and relative)
Total White Blood Cell Count
Reticulocyte Haemoglobin
Reticulocyte Sub-Populations (H-, M- and L-reticulocytes)

Clinical Chemistry

All animals: prior to dosing (Day 1) and at study termination (Day 30: Groups 3 to 6; Day 43: Groups 1 and 2).

Approximately 2 ml of whole blood will be taken from each dog per time point.
Sodium
Potassium
Chloride
Calcium
Inorganic phosphorus
Glucose
Urea
Total cholesterol
Triglycerides
Total bilirubin
Total protein
Albumin
Globulin (calculated)
Albumin/globulin ratio
Creatinine
Alkaline phosphatase
Aspartate aminotransferase
Alanine aminotransferase
Gamma glutamyl transferase.

Pharmacokinetics

Animals examined: all animals.

Blood was withdrawn from the jugular vein of the unanaesthetized, manually restrained animal. Approximately 2 ml of whole blood were taken from each dog per time-point into containers with heparin anticoagulant placed on wet ice. Plasma samples were obtained by centrifugation at approximately 3000 rpm for ten minutes and transferred to polypropylene tubes. The plasma samples were stored deep-frozen (approximately −20° C.) pending dispatch to the auxiliary Testing Facility 1.

Samples were taken at the following time points:

| Groups 1 and 2 | |
|---|---|
| Day 1 | Pre-dose, 6 and 24 hours after dosing |
| Day 2 | 24 and 36 hours after dosing on Day 1 |
| Days 3, 3, 4, 5, 6, 7 and 8 | Once daily |
| Day 15 (pre-dose) | Second dose |
| Day 16 | Once daily |
| Day 29 (pre-dose) | Third dose |
| Day 30 and 43 | Once daily |
| Groups 3 to 6 | |
| Day 1 | Pre-dose, 6 and 24 hours after dosing |
| Day 2 | 24 and 36 hours after dosing on Day 1 |
| Days 3, 4, 5, 6, 7 and 8 | Once daily |
| Day 15 (pre-dose) | Second dose |
| Day 16 and 30 | Once daily |

Pharmacodynamic Data Evaluation

The group mean values for all pharmacodynamic (haematology) parameters were plotted (FIGS. 5 to 8).

EXAMPLE 5

Pharmacokinetic/Pharmacodynamic Cross-Over G-CSF Formulation Study by Subcutaneous Administration in Non-Immunosuppressed Male Beagle Dogs

| Test System | |
|---|---|
| Species/breed: | Beagle dogs |
| Supplier: | Harlan France, Z. I. du Malcourlet, R.N. 9, B.P. 98, 03800 GANNAT, France |
| Number of animals in study: | 6 dogs |
| Age (approximate) at initiation of study: | 5 to 7 months |
| Body weight range (approximately) at initiation of study: | 9 to 11 kg |

This study is conducted in dogs to evaluate various formulations of GCSF (Granulocyte colony stimulating factor). The number of dogs used was the minimum number necessary to provide scientifically valid results for each of the formulations examined. No acceptable in vitro models are available. Purpose-bred beagle dogs are routinely used for the conduct of pharmacokinetic, pharmacodynamic and toxicological studies to meet regulatory requirements.

Animal Husbandry

Housing: one room for the study, in an air-conditioned building

Temperature: 19 to 25° Celsius (target range)

Relative humidity:>40 %

Air changes: Minimum 10 air changes per hour

Lighting cycle: 12 hours light (artificially)/12 hours dark.

Caging: animals housed singly in pens (1.44 m²)

Diet: pelleted complete commercial diet (Diet 125C1, UAR), analyzed for the absence of chemical and bacteriological contaminants.

Quantity distributed: 300 g/animal/day (food is offered after dosing on treatment days and at approximately the same time of day on other study days).

Animals are fasted overnight before sampling for clinical laboratory determinations and before necropsy. Due to the nature of the sampling schedule, not all of the pharmacokinetic samples are taken under fasted conditions.

Water: mains drinking water, ad libitum, analyzed at least once a year for chemical contaminants and at least twice a year for bacterial contaminants.

Contaminants: no contaminants are known to be present in the diet or water at levels which might interfere with achieving the objective of the study. Certificates of analysis for the diet and for the water is maintained in the archives of the testing facility.

Pre-Treatment Procedures

Animal health procedure:

Standard canine vaccination and anti-parasite treatment performed by the supplier;

Clinical examination for ill health on arrival;

Full clinical examination during the acclimatization period.

Acclimatization period:

Two weeks minimum between animal arrival and start of treatment.

Identification of the animals:

Using tattoo on the pinna and microchip implants: Electronic Laboratory Animal Monitoring System ELAMS (Bio Medic Data Systems) Identification numbers.

| Group Number | Color Code | Animal Numbers |
|---|---|---|
| 1 | Green | 391 to 393 |
| 2 | Blue | 394 to 396 |

Experimental Design

Allocation to treatment group: performed during the acclimatization period: random allocation procedure based on body weight classes.

Animals are assigned to the following groups:

| | Treatment | | GCSF Dose (µg/kg/ administration)* | Number of males |
|---|---|---|---|---|
| Group | Day 1 | Day 15 | | |
| 1 | Test Article A | Test Article B | 70 | 3 |
| 2 | Test Article B | Test Article A | 70 | 3 |

*the dose level used for the second administration (day 15) is confirmed following the analysis of the first week's pharmacokinetic samples: the dose levels are defined by protocol amendment.

Article A: GCSF, Lot No. 14901-185, Concentration: 1.164 mg/ml formulated as described herein.

Article B: CMC-GCSF, Lot No. 15849-136-1, Concentration: 0.60 mg/ml formulated as described herein.

The dose volumes required to perform the above regimen are as follows:

| | GCSF Dose (µg/kg/administration) | | Number of |
|---|---|---|---|
| Group | Day 1 | Day 14 | males |
| 1 | 0.60 | To be defined by protocol amendment | 3 |
| 2 | 0.117 | To be defined by protocol amendment | 3 |

Rationale for Dose Selection: The doses were selected based on existing data obtained from formulations evaluated in previous studies.

Administration Of Test Articles

Method: bolus injection using a sterile syringe and needle introduced subcutaneously after local disinfection with an aqueous solution of ethyl alcohol. Two injection sites in the dorsal cervical/interscapular regions is in rotation.

Volume administered: dependent on dosing regimen. Individual dose volumes are calculated on Days 1 and 15 to two decimal places according to the latest recorded body weight; these volumes are recorded in the study data. The syringes containing the dosing solution are weighed before and after administration in order to calculate the actual individual delivered dose.

Rationale for choice of route of administration: The subcutaneous route was selected as this is the route of administration in humans Route: Subcutaneous Frequency: Once on Days 1 and 15.

Duration: Two administrations over the course of the study (Days 1 and 15)

Morbidity/Mortality

Animals are observed at lease twice daily. Any animal judged to be in a moribund condition is bled for haematological, clinical chemistry and pharmacokinetic determinations and then euthanized.

Clinical Signs

Animals are observed daily. During the treatment period, animals are examined before and at least once after dosing to detect any clinical signs or reaction to treatment. The injection sites are observed daily. A full clinical examination is performed before the initiation of treatment.

Body Weight

Individuals weighing once weekly, starting two weeks before initiation of treatment.

Blood Collection

Blood:

Withdrawn from the jugular vein of on unanaesthetized, manually restrained animal.

Collection of samples:

Haematology parameters: EDTA

Clinical Chemistry parameters: Without anticoagulant

Haematology

All animals: Twice prior to dosing (Day-7 and prior to dosing on Day 1), and at the following time-points:

| Day 1 | 6, 12 and 16 hours after treatment 1 |
|---|---|
| Day 2 | 24 and 36 hours after treatment 1 |
| Day 3 | 48 hours after treatment 1 |
| Day 4 | 72 hours after treatment 1 |

| Day 5 | 96 and 108 hours after treatment 1 |
| Day 15 | 6, 12 and 16 hours after treatment 2* |
| Day 16 | 24 and 36 hours after treatment 2* |
| Day 17 | 48 hours after treatment 2* |
| Day 18 | 72 hours after treatment 2* |
| Day 19 | 96 and 108 hours after treatment 2* |

*The sampling schedule used for the second administration (Day 15) is confirmed following the analysis of the first week's pharmacodynamic data; the time-points are defined by protocol amendment.

Approximately 0.5 ml of whole blood is taken from each dog per time-point.
Total white blood cell count
Differential white blood cell count (neutrophils, lymphocytes, monocytes, eosinophils and basophils).

Quality Control Of Haematological Data

The quality of haematological data is controlled as follows:

Controls are run before and after each initial run of blood samples (repeat analysis not included). For each control batch, a mean and standard deviation are calculated per time-point for the entire in-house life span of each given batch used during the course of the study. The batch numbers are also recorded. The ADVIA, used to perform haematological determinations is operated in CBC/DIFF mode in order to collect differential white blood cell data.

Clinical Chemistry

Performed on all animals prior to dosing on Day 1 and at termination (Day 19). Approximately 2 ml of whole blood is taken from each dog per time-point.

Sodium
Potassium
Chloride
Calcium
Inorganic phosphorus
Glucose
Urea
Total cholesterol
Total nilirubin
Total protein
Albumin
Globulin (calculated)
Albumin/globulin ratio
Creatinine
Triglycerides
Alkaline phosphatase
Aspartate aminotransferase
Alanine aminotransferase
Gamma glutamyl transferase Pharmacokinetics Animals examined: all animals Blood: withdrawn from the jugular vein of the unanaesthatized, manually restrained animal. Approximately 2 ml of whole blood is taken from each dog per time-point into containers with heparin anticoagulant placed on wet ice. Plasma samples are obtained by centrifugation at approximately 3000 rpm for ten minutes and transferred to polypropylene tubes. The plasma samples are stored in deep-frozen (approximately −20 degrees)

Samples are collected from all animals at the following time-points

| Day 1 | Pre-dose, 2, 4, 6, 8, 10, 12 and 16 hours after treatment 1 |
| Day 2 | 24 and 36 hours after treatment 1 |
| Day 3 | 48 hours after treatment 1 |
| Day 4 | 72 hours treatment 1 |
| Day 5 | 96 and 108 hours after treatment 1 |
| Day 15 | Pre-dose, 2, 4, 6, 8, 10, 12 and 16 hours after treatment 2* |
| Day 16 | 24 and 36 hours after treatment 2* |
| Day 17 | 48 hours after treatment 2* |
| Day 18 | 72 hours after treatment 2* |
| Day 19 | 96 and 108 hours after treatment 2* |

*the sampling schedule for the second administration (Day 15) is confirmed following the analysis of the first week's pharmacodynamic samples; the time-points are defined by protocol amendments.

Data Evaluation

Pharmacodynamic Data Evaluation:

The group mean values for all phamacodynbamic (haematology) parameters is plotted as graphs. The areas under the parameter-time curves ($AUC_{(0-last)}$ of the baseline adjusted parameter) are estimated by the linear trapezoidal rule according to Bailer (1988). Reference for this technique is A. J. Bailer, *J. Pharmacokin. Biopharm.*, (1988) 1:303–309. Only positive areas under the mean parameter-time curves are calculated using the following rules:

1) each individual parameter baseline is determined on a case-by-case basis using the value from either Day 1 or Day 3, the lower value of the two setting the baseline.
2) Where the curve falls below the baseline, the time-point(s) concerned are assigned the baseline value; this only applies to ($AUC_{(0-last)}$ calculation.

Arithmetic group mean and standard deviation values are calculated for each parameter and its respective ($AUC_{(0-last)}$.

Pharmacokinetic Data Evaluation

The maximum mean plasma concentrations ($C_{(max)}$) and their times of occurrence ($T_{(max)}$) are the observed values. The areas under plasma concentration-time curves ($AUC_t$), and their variances, are estimated by the linear trapezoidal rule according to Bailer (1988). Where appropriate, terminal rate constants (k) are estimated by fitting a linear regression of log mean concentration against time using data points randomly distributed about a single straight line. Terminal half-lives are calculated as Ln2/k together with clearance (Cl+achieved dose/$AUC_t$). Reference for this technique is A. J. Bailer, *J. Pharmacokin. Biopharm.*, (1988) 16:303–309.

What is claimed is:

1. A pharmaceutical formulation comprising:
    a) a pharmaceutically active amount of erythropoietin;
    b) a pharmaceutically acceptable pH buffering agent to provide a pH in a range of about pH 6 to about pH 9;
    c) a tonicity agent in a concentration range of about 0 to about 200 millimolar; and
    d) sodium carboxymethyl ether cellulose in a concentration range of about 0.5% to about 7% total formula weight, said sodium carboxymethyl ether cellulose having a molecular weight in a range of about 50,000 daltons to about 1,000,000 daltons.

2. The formulation of claim 1 wherein the erythropoietin is selected from the group consisting of recombinant human erythropoietin, epoietin alfa, epoietin omega, darbepoetin alfa, and PEG conjugated erythropoietin.

3. The formulation of claim 1 wherein the pH buffering agent is present in the formulation at a concentration in the range of about 10 mM to about 30 mM and wherein the pH buffering agent is a sodium phosphate monobasic/sodium phosphate dibasic buffer system.

4. The formulation of claim 1 wherein the tonicity agent is selected from the group consisting of NaCl, KCl, and glycine.

5. The formulation of claim 1 wherein the tonicity agent is NaCl at a concentration of about 75 mM to about 125 mM.

6. The formulation of claim 1 wherein the pH of the formulation is in the range of about 6.5 to about 7.4.

* * * * *